(12) United States Patent
Sandrin et al.

(10) Patent No.: US 11,808,898 B2
(45) Date of Patent: Nov. 7, 2023

(54) METHOD FOR MEASURING AN ULTRASONIC ATTENUATION PARAMETER GUIDED BY HARMONIC ELASTOGRAPHY, PROBE AND DEVICE FOR THE IMPLEMENTATION OF THE METHOD

(71) Applicant: ECHOSENS, Paris (FR)

(72) Inventors: Laurent Sandrin, Bourg-la-Reine (FR); Stéphane Audiere, Paris (FR)

(73) Assignee: ECHOSENS, Paris (FR)

( * ) Notice: Subject to any disclaimer, the term of this patent is extended or adjusted under 35 U.S.C. 154(b) by 718 days.

(21) Appl. No.: 16/977,369

(22) PCT Filed: Feb. 26, 2019

(86) PCT No.: PCT/EP2019/054656
§ 371 (c)(1),
(2) Date: Sep. 1, 2020

(87) PCT Pub. No.: WO2019/166393
PCT Pub. Date: Sep. 6, 2019

(65) Prior Publication Data
US 2021/0048518 A1    Feb. 18, 2021

(30) Foreign Application Priority Data
Mar. 2, 2018 (FR) ...................... 1851822

(51) Int. Cl.
*A61B 8/00* (2006.01)
*G01S 7/52* (2006.01)
*A61B 8/08* (2006.01)

(52) U.S. Cl.
CPC ............ *G01S 7/52042* (2013.01); *A61B 8/08* (2013.01); *A61B 8/485* (2013.01); *G01S 7/52079* (2013.01)

(58) Field of Classification Search
CPC .. A61B 8/00; A61B 8/08; A61B 8/485; G01S 7/00; G01S 7/52; G01S 7/52042; G01S 7/52079
See application file for complete search history.

(56) References Cited

U.S. PATENT DOCUMENTS 11,457,895 B2 * 10/2022 Audiere ................ A61B 8/085
2012/0226158 A1    9/2012 Greenleaf et al.
(Continued)

FOREIGN PATENT DOCUMENTS

EP    2 739 211 A1    6/2014
JP    2005-534455 A    11/2005
(Continued)

OTHER PUBLICATIONS

Notice of Reasons for Refusal as issued in Japanese Patent Application No. 2020-545644, dated Jan. 31, 2023.
(Continued)

Primary Examiner — Nguyen Q. Ha
(74) Attorney, Agent, or Firm — Pillsbury Winthrop Shaw Pittman LLP (57) ABSTRACT

A method for measuring an ultrasonic attenuation parameter guided by harmonic elastography including applying, using a vibrator included in a probe in contact with a viscoelastic medium, of a continuous low frequency vibration, the continuous low frequency vibration generating an elastic wave within the viscoelastic medium and generating, during the propagation of the elastic wave, using an ultrasonic transducer in contact with the viscoelastic medium, a series of ultrasonic acquisitions, the series of ultrasonic acquisitions including groups of ultrasonic acquisitions, the groups of ultrasonic acquisitions being generated with a repetition rate, each group of ultrasonic acquisitions including at least one acquisition; the ultrasonic attenuation parameter being
(Continued)

measured from the ultrasonic acquisitions realised during the application of the continuous low frequency vibration.

16 Claims, 6 Drawing Sheets

(56) References Cited

U.S. PATENT DOCUMENTS

| | | | |
|---|---|---|---|
| 2012/0269414 A1 | 10/2012 | Zha et al. | |
| 2012/0271166 A1 | 10/2012 | Shao et al. | |
| 2014/0147013 A1 | 5/2014 | Shandas et al. | |
| 2015/0141821 A1* | 5/2015 | Yoshikawa | A61B 8/469 600/438 |
| 2015/0374338 A1* | 12/2015 | Sandrin | A61B 8/485 600/438 |

FOREIGN PATENT DOCUMENTS

| | | |
|---|---|---|
| JP | 2008-126079 A | 6/2008 |
| JP | 2011-189042 A | 9/2011 |
| JP | 2013-505040 A | 2/2013 |
| WO | WO 2011/004661 A1 | 1/2011 |
| WO | WO 2013/017532 A1 | 2/2013 |
| WO | WO 2016/069750 A1 | 5/2016 |

OTHER PUBLICATIONS

International Search Report as issued in International Patent Application No. PCT/EP2019/054656, dated Mar. 26, 2019.

Sandrin, L., et al, "Transient Elastography: a New Non-Invasive Method for Assessment of Hepatic Fibrosis," Ultrasound in Medicine and Biology, vol. 29, (2003), pp. 1705-1713.

Sasso, M., et al., "Liver Steatosis Assessed by Controlled Attenuation Parameter (CAP) Measured With the XL Probe of the Fibroscan: a Pilot Study Assessing Diagnostic Accuracy," Ultrasound in Medicine and Biology, (2015), pp. 1-12.

Sasso, M., et al., "Controlled Attenuation Parameter (CAP): a Novel VCTE™ Guided Ultrasonic Attenuation Measurement for the Evaluation of Hepatic Steatosis: Preliminary Study and Validation in a Cohort of Patients With Chronic Liver Disease From Various Causes," Ultrasound in Medicine and Biology, vol. 36, No. 11, (2010), pp. 1825-1835.

Sasso, M., et al., "The controlled attenuation parameter (CAP): A novel tool for the non-invasive evaluation of steatosis using Fibroscan®," Clinics and Research in Hepatology and Gastroenterology, vol. 36, (2012), pp. 13-20.

* cited by examiner

METHOD FOR MEASURING AN ULTRASONIC ATTENUATION PARAMETER GUIDED BY HARMONIC ELASTOGRAPHY, PROBE AND DEVICE FOR THE IMPLEMENTATION OF THE METHOD

CROSS-REFERENCE TO RELATED APPLICATIONS

This application is the U.S. National Stage of PCT/EP2019/054656, filed Feb. 26, 2019, which in turn claims priority to French patent application number 1851822 filed Mar. 2, 2018. The content of these applications are incorporated herein by reference in their entireties.

TECHNICAL FIELD

The invention belongs to the field of the measurement of ultrasonic attenuation and more specifically to the use of harmonic elastography to guide the determination of the ultrasonic attenuation of a medium having an ultrasonic signal after ultrasonic illumination. The invention firstly relates to a method for measuring an ultrasonic attenuation parameter guided by harmonic elastography. The invention secondly relates to a probe for measuring an ultrasonic attenuation parameter guided by harmonic elastography. The invention thirdly relates to a device for the measurement of the ultrasonic attenuation guided by harmonic elastography. The method for measuring the ultrasonic attenuation guided by harmonic elastography is particularly suited for determining the properties of a viscoelastic medium such as a human or animal liver.

PRIOR ART

It is known that ultrasonic attenuation is correlated with the amount of fat contained in the liver. It may thus be used to measure the amount of steatosis in the liver.

The Applicant has developed and commercialised a device that quantifies in a non-invasive manner ultrasonic attenuation called CAP. The technique used is the measurement of the ultrasonic attenuation guided by vibration controlled transient elastography (VCTE). The VCTE technique is described in the document "Transient Elastography: a new non-invasive method for assessment of hepatic fibrosis" of L. Sandrin et al., published in Ultrasound in Medicine and Biology, Vol. 29, pages 1705-1713, 2003. The study of ultrasonic signals acquired for the measurement of elasticity makes it possible to work back to the ultrasonic attenuation of the medium as is explained in the documents:

- "The controlled attenuation parameter (CAP): A novel tool for the non-invasive evaluation of steatosis using Fibroscan®" of M. Sasso et al., published i n Clinical Research in Hepatology and Gastroenterology, 2011;
- "Controlled Attenuation Parameter (CAP): A Novel VCTE™ Guided Ultrasonic Attenuation Measurement for the Evaluation of Hepatic Steatosis: Preliminary Study and Validation in a Cohort of Patients with Chronic Liver Disease from Various Causes" of M. Sasso et al., published in Ultrasound in Medicine and Biology, 2010;
- "Liver steatosis assessed by controlled attenuation parameter (cap) measured with the xl probe of the Fibroscan: a pilot study assessing diagnostic accuracy" of M. Sasso et al. published in Ultrasound in Medicine and Biology, 2015.

The device implementing this technique, called Fibroscan®, is capable of measuring the elasticity and the ultrasonic attenuation of the human liver in a rapid, non-invasive and reproducible manner. In Fibroscan, the measurement of the ultrasonic attenuation (CAP) is validated by the measurement of elasticity: when the measurement of elasticity is valid, the associated CAP value is considered as valid. It thus does not involve a guiding a priori but a validation a posteriori. To measure ultrasonic attenuation with precision, Fibroscan validates the measurement of CAP from the pulse elastography result.

In such a transient elastography device, the pulse shear wave is generated by a vibrator placed in contact with the medium to characterise. The propagation of the shear wave is next monitored using a series of ultrasonic acquisitions realised by an ultrasonic transducer with a high repetition rate. Each ultrasonic acquisition corresponds to at least one ultrasonic emission. Each ultrasonic emission may be associated with the detection and the recording on the go of the echoes generated by the reflective particles present in the studied medium for a defined range of depths. The reflected ultrasonic signals are processed by correlation to work back to the movements of the tissue generated by the propagation of the shear wave as a function of time and the position in the medium. The study of these movements makes it possible to work back to the propagation velocity of the shear wave within the viscoelastic medium then to the elasticity.

The measurement of CAP (ultrasonic attenuation) by the VCTE technique has several limitations.

The first drawback of the measurement of CAP (ultrasonic attenuation) by the VCTE technique is the difficulty of predicting that the probe is effectively placed facing the liver. Indeed, it is necessary to carry out a valid measurement by pulse elastography to obtain a measurement of the ultrasonic attenuation.

The second drawback of the measurement of CAP by the VCTE technique is the cost of the device, which requires the use of a pulse vibration, the cost of which is high.

The third drawback of the measurement of CAP by the VCTE technique is the necessity of carrying out around ten or so elasticity measurements by pulse elastography of which the individual duration is at least 1 second including the computation time, which leads to an examination time of around one minute.

Today it is possible to use ultrasounds to guide the positioning of the vibrator for transient elastography. For example, it is possible to use ultrasonic imaging or a targeting tool such as the one described in the patent application EP2739211 A1. However, these solutions are not satisfactory because they do not make it possible to predict directly that the probe is correctly positioned facing the studied organ. Furthermore, these techniques are very operator dependent. Finally the ultrasonic signals may turn out to be not very specific of the liver.

Furthermore, so-called harmonic elastography techniques exist. These techniques are based on the application of a continuous vibration having a frequency comprised between 30 Hz and 100 Hz. The elastic waves created within the medium are quasi-stationary waves, superimpositions of shear waves and compression waves which are not as efficient as pulse elastography techniques for the precise measurement of viscoelastic properties but which use nevertheless shear waves and can measure the propagation thereof.

Finally it is known that low frequency shear waves propagate well in the liver. This observation is true for pulse and harmonic shear waves.

Furthermore, the harmonic elastography technique may be used to guide treatment methods. It involves for example treating localised tumours by the harmonic elastography technique by means of hyperthermia type methods.

TECHNICAL PROBLEM

No technique for measuring ultrasonic attenuation ensures optimal guiding in real time of the ultrasonic probe used with respect to the tissue to characterise. The result is that the measurement may turn out to be difficult to carry out given the impossibility of affirming that the studied organ is correctly situated facing the probe. This is not favourable to an implementation with devices of small size and that are easy to use.

SUMMARY OF THE INVENTION

To resolve at least partially these problems, the present invention describes a novel technique for measuring an ultrasonic attenuation parameter which is guided by harmonic elastography.

The present invention firstly relates to a method for measuring an ultrasonic attenuation parameter guided by harmonic elastography including a step of application, using a vibrator comprised in a probe in contact with a viscoelastic medium, of a continuous low frequency vibration, the continuous low frequency vibration generating an elastic wave within the viscoelastic medium and generation, during the propagation of the elastic wave, using an ultrasonic transducer in contact with the viscoelastic medium, of a series of ultrasonic acquisitions, said series of ultrasonic acquisitions including groups of ultrasonic acquisitions, the groups of ultrasonic acquisitions being generated with a repetition rate, each group of ultrasonic acquisitions including at least one acquisition;

the ultrasonic attenuation parameter being measured from the ultrasonic acquisitions.

According to one embodiment the ultrasonic acquisitions are realised during the application of the continuous low frequency vibration.

Measurement of ultrasonic attenuation guided by harmonic elastography is taken to mean a method including at least one step of application of a continuous vibration and the measurement of a parameter reflecting the ultrasonic attenuation. In other words, the method according to the invention includes both a generation of a continuous vibration, which is characteristic of a harmonic elastography technique, and the measurement of a parameter reflecting the ultrasonic attenuation.

Ultrasonic attenuation is taken to mean any parameter that reflects ultrasonic attenuation: Broadband Ultrasound Attenuation (BUA, in dB/cm/MHz), the attenuation measured at a particular frequency (in dB/cm), the Controlled Attenuation Parameter (CAP), etc.

Continuous low frequency vibration is taken to mean continuous reproduction of a wave form pattern. This pattern may for example be a perfect sinusoid; this is then known as monochromatic vibration. The vibration may also be constituted by the reproduction of an arbitrary pattern. The continuous vibration is interrupted to stop the measurement process or when the measurement conditions are no longer satisfactory. The measurement conditions being able to be for example a condition on the contact force with the studied medium. The central frequency of the continuous low frequency vibration is comprised between 5 and 500 Hz.

Elastic wave is taken to mean the superimposition of compression waves and shear waves.

Ultrasonic acquisition is taken to mean the emission of an ultrasonic shot. Said ultrasonic emission may be associated with the detection and the recording on the go of the echoes generated by the reflective particles present in a defined range of depths of the studied medium.

The series of ultrasonic acquisitions is thus formed by a repetition of groups of acquisitions. A group of acquisitions includes at least one ultrasonic acquisition. The groups of acquisitions are emitted or generated with a first repetition rate. The first repetition rate is also called inter-group repetition rate. The first repetition rate is typically comprised between 5 and 500 Hz.

When each group of acquisitions is formed by at least two ultrasonic acquisitions, the ultrasonic acquisitions forming a same group are emitted or generated with an intra-group repetition rate typically comprised between 500 Hz and 100 kHz.

Advantageously, the use of a low repetition rate during the application of the continuous vibration makes it possible to measure the displacements of the viscoelastic tissue while limiting the acoustic energy sent into the tissue itself so as not to exceed the peak and average acoustic power limits.

The term displacement is considered in the wider sense in this document. It encompasses any movement parameter such as the displacement, the velocity, the deformation, the deformation rate, the deformation velocity and any mathematical transformation applied to these parameters.

During the application of the continuous vibration, an elastic wave is generated within the viscoelastic medium.

The series of ultrasonic acquisitions is used to study the propagation of the elastic wave within the viscoelastic medium. It is possible to detect the echoes or ultrasonic signals reflected by the viscoelastic medium and to compute, from these reflected ultrasonic signals, the displacements of the viscoelastic medium caused by the propagation of the elastic wave within the viscoelastic medium generated by the continuous vibration.

As an example, it is possible to compute the displacements of the viscoelastic medium by applying a correlation technique to the ultrasonic acquisitions composing a same group of acquisitions of the series of ultrasonic acquisitions.

It is important to note that the propagation of the elastic wave evolves as a function of the position of the probe in contact with the studied medium.

It is then possible to measure a property of the propagation of the elastic wave within the medium and to compute in real time a positioning indicator from the measured properties. Ideally this real time positioning indicator is displayed in real time to guide the operator in order that he finds the best position for the probe. Examples of measured properties for computing the positioning indicator are the amplitude and the phase of the elastic wave, measured as a function of depth in the tissue to characterise. It is also possible to compute the phase velocity of the elastic wave.

In the remainder of this document "real time positioning indicator" and "positioning indicator" refer to the same real time positioning indicator.

Real time is taken to mean an indicator of which the display is regularly refreshed during the examination. In general, the refresh rate is around 20 Hz but may also be of the order of 1 Hz.

In other words, the positioning indicator gives a probability of the presence of the viscoelastic medium to characterise facing the ultrasonic transducer.

It is important to note that the continuous vibration is above all used to verify the positioning of the probe used for the measurement of the ultrasonic attenuation. As an example, the continuous vibration may be used to verify the presence of the hematic parenchyma facing the probe. In other words, during the step of application of a continuous vibration, the indirect measurement of the viscoelastic properties of the medium is possible but not indispensable. However, an elasticity value may effectively be deduced from the phase velocity of the elastic wave. Indeed, the measurement of the displacements generated in the viscoelastic medium by said propagation next makes it possible to work back to the propagation velocity of the elastic wave. If the hypothesis is made that the elastic wave is mainly a shear wave, it is then possible to compute the elasticity of the medium using the formula $E=3\eta V_s^2$ where E is the elasticity or Young's modulus, $\eta$ the density and $V_s$ the velocity of the elastic wave.

The method for guiding a measurement of ultrasonic attenuation by harmonic elastography according to the invention thus makes it possible to predict if the positioning of the probe is favourable using a harmonic elastography technique. It involves a guiding. The measurements of the ultrasonic attenuation carried out over time may be stored in a memory. In particular each measurement of ultrasonic attenuation may be associated with a quality coefficient. In general the quality coefficient will be a coefficient comprised between 0 and 1. The value 0 corresponding to a poor quality and the value 1 to a very good quality of measurement.

The computation of the quality coefficient may be carried out from the propagation properties of the elastic wave. It may also include the characteristics of the ultrasonic signals, and quality criteria emanating from the computation of the ultrasonic attenuation.

The final measurement of ultrasonic attenuation retained may be computed from the measurements of ultrasonic attenuation and quality coefficients stored in the memory.

In other words, guiding by harmonic elastography makes it possible to associate with each measurement of ultrasonic attenuation a quality coefficient and to guide the positioning of the probe facing the tissue to characterise by providing to the operator a positioning indicator predictive of the presence of the studied organ.

As an example, the measurement of ultrasonic attenuation retained is the average of the measurements of ultrasonic attenuation stored, weighted by their quality coefficients. The total number of measurements of ultrasonic attenuation may typically be comprised between 1 and several thousand measurements. For example, if the measurements are accumulated for 60 seconds at a rate of 20 measurements per second, N will be equal to 1200.

Advantageously, the method for guiding a measurement of ultrasonic attenuation by harmonic elastography according to the invention makes it possible to carry out a measurement of ultrasonic attenuation of the tissue to characterise in a reliable and reproducible manner while ensuring an optimal positioning of the probe in a simple and precise manner thanks to a harmonic elastography technique.

Advantageously, the method for guiding a measurement of ultrasonic attenuation by harmonic elastography according to the invention makes it possible to reduce manufacturing costs by the use of a simpler vibratory system simpler than in pulse elastography.

Advantageously, the method for guiding a measurement of ultrasonic attenuation by harmonic elastography according to the invention makes it possible to provide a real time positioning indicator to the operator.

The method for guiding a measurement of ultrasonic attenuation by harmonic elastography according to the invention may also have one or more of the characteristics below, considered individually or according to all technically possible combinations thereof:

- the method according to the invention further includes a step of determination, from the series of ultrasonic acquisitions, of at least one property of the propagation of the elastic wave within the viscoelastic medium;
- the property of propagation of the elastic wave within the viscoelastic medium is used to compute a real time positioning indicator of the probe with respect to the viscoelastic medium to study;
- the method according to the invention further includes a step of displaying in real time the real time positioning indicator;
- the step of application of a continuous low frequency vibration is only triggered if the contact force between the vibrator and the viscoelastic medium is above a predetermined lower threshold;
- the step of application of a continuous low frequency vibration is only triggered if the contact force between the vibrator and the viscoelastic medium is above a predetermined lower threshold and below a predetermined upper threshold;
- the series of ultrasonic acquisitions is formed by a repetition of groups including at least two ultrasonic acquisitions having an intra-group repetition rate comprised between 500 Hz and 10 kHz and a repetition rate comprised between 10 Hz and 10 kHz;
- the repetition rate is lower than the continuous vibration frequency;
- a parameter of the ultrasonic wave that reflects the ultrasonic attenuation is computed and displayed;
- the ultrasonic attenuation parameter is an instantaneous parameter and a quality coefficient associated with the measurement of the instantaneous ultrasonic attenuation parameter is computed from a property of the propagation of the elastic wave within the viscoelastic medium and/or properties of the ultrasonic wave; an instantaneous parameter is taken to mean a measurement obtained at each ultrasonic acquisition or from a single ultrasonic acquisition;
- an average ultrasonic attenuation parameter is computed from a plurality of instantaneous ultrasonic attenuation parameters and quality coefficients associated with each instantaneous ultrasonic attenuation parameter;
- the ultrasonic attenuation parameters, associated or not with quality coefficients computed on the basis of the propagation properties of the elastic wave within the viscoelastic medium, are stored in a memory;
- the predetermined lower threshold of contact force for the application of the continuous vibration is typically chosen equal to 1 N;
- the frequency of the low frequency vibration, cSWF, applied by the vibrator is comprised between 5 and 500 Hz;
- the amplitude of the low frequency vibration applied by the vibrator is comprised between 10 μm and 5 mm;
- the series of ultrasonic acquisitions is formed by a repetition of groups including at least two ultrasonic acquisitions having an intra-group repetition rate comprised between 500 Hz and 10 kHz and a first repetition rate comprised between 10 Hz and 10 kHz;
- the first repetition rate is lower than the continuous vibration frequency;
- the ultrasonic attenuation parameter is selected from the BUA
the attenuation of a particular ultrasonic frequency;
the ultrasonic controlled attenuation parameter (CAP);
the propagation property of the elastic wave is delivered to the operator;
the propagation property of the elastic wave is selected from:
the amplitude of the elastic wave;
the phase of the elastic wave;
the Young's modulus of the viscoelastic medium;
the shear modulus of the viscoelastic medium;
the shear velocity of the viscoelastic medium.

The present invention also relates to a probe for the implementation of the hybrid elastography method according to the invention. The probe according to the invention includes:
A vibrator configured to apply to the viscoelastic medium a continuous low frequency vibration, the continuous low frequency vibration generating an elastic wave within the viscoelastic medium;
An ultrasonic transducer configured to emit a series of ultrasonic acquisitions, said series of ultrasonic acquisitions including groups of ultrasonic acquisitions, the groups of ultrasonic acquisitions being generated with a repetition rate, each group of ultrasonic acquisitions including at least one acquisition;
Means for computing and displaying in real time a positioning indicator of the probe, said positioning indicator being computed from a propagation property of the elastic wave, said propagation property of the elastic wave being determined from the series of ultrasonic acquisitions;
the ultrasonic attenuation parameter being measured from the ultrasonic acquisitions realised during the application of the continuous low frequency vibration.

According to one embodiment, said probe is further configured to apply the continuous vibration when the contact force between the probe and the viscoelastic medium is above a predetermined value.

The probe according to the invention enables the implementation of the method according to the invention.

The ultrasonic transducer is used to send the series of ultrasonic acquisitions within the viscoelastic medium. The same ultrasonic transducer detects the ultrasonic signals reflected at each acquisition. The reflected ultrasonic signals are next processed to detect the displacements of the viscoelastic medium generated by the elastic waves.

Computing means is taken to mean at least one microprocessor and one memory intended to store the ultrasonic acquisitions and the results of the computations such as a positioning indicator of the probe or a propagation property of the elastic wave.

Display means is taken to mean a screen or an indicator configured to display the positioning indicator. The indicator may be for example a light indicator such as a diode or a sound indicator.

The hybrid elastography probe according to the invention may also have one or more of the characteristics below, considered individually or according to all technically possible combinations thereof:
the vibrator is an electric motor or an audio reel or an electrodynamic actuator;
the ultrasonic transducer is mounted on the axis of the vibrator;
the probe according to the invention further includes means for triggering the accumulation of measurements;
the ultrasonic transducer is circular with a diameter comprised between 2 mm and 15 mm;
the ultrasonic transducer has an operating frequency comprised between 1 MHz and 15 MHz;
the probe is configured to compute an average ultrasonic attenuation parameter, said average ultrasonic attenuation parameter being computed from a multiplicity of instantaneous ultrasonic attenuation parameters and quality coefficients associated with the instantaneous ultrasonic attenuation parameters;
the ultrasonic transducer is a convex abdominal probe.

The present invention also relates to a hybrid elastography device implementing the hybrid elastography method according to the invention.

Such a hybrid device according to the invention includes:
A probe according to the invention;
A central unit connected to the probe and including at least computing means for processing the reflected ultrasonic signals, display means and control and/or input means.

In a particular embodiment, the central unit is placed within the probe.

LIST OF FIGURES

Other characteristics and advantages of the invention will become clear from the description that is given thereof below, for indicative purposes and in no way limiting, with reference to the appended figures among which.

DETAILED DESCRIPTION

Figure 1:
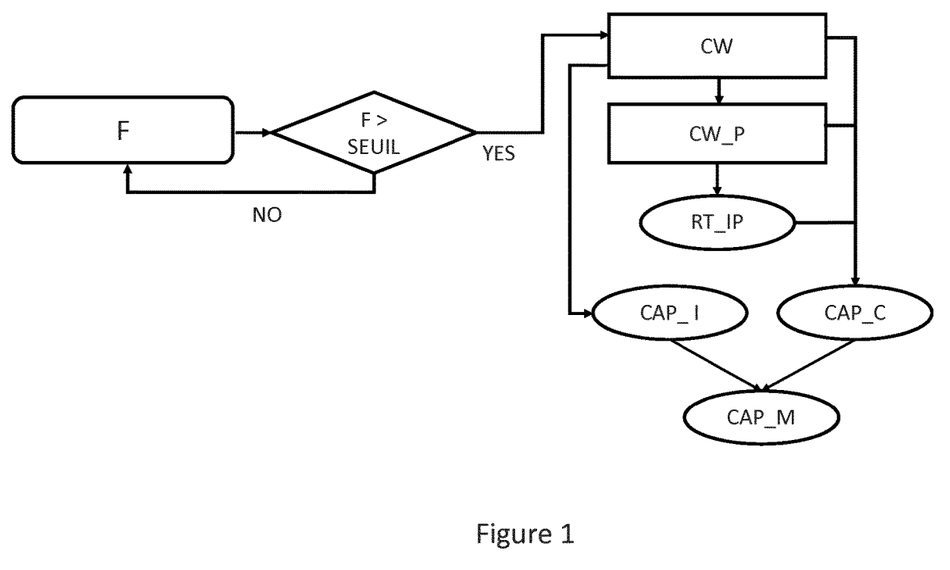
FIG. 1 illustrates the steps of the hybrid elastography method according to the invention.

FIG. 1 illustrates the steps of the hybrid elastography method P according to the invention.

The method P according to the invention includes a step CW of applying a continuous low frequency vibration using a vibrator comprised in a probe in contact with the viscoelastic medium.

The central frequency of the continuous vibration is comprised between 5 and 500 Hz.

The step CW of the method P further includes the generation, by the ultrasonic transducer, of a series of ultrasonic acquisitions. The series of ultrasonic acquisitions includes groups of ultrasonic acquisitions. The groups of ultrasonic acquisitions are emitted with a repetition rate comprised between 5 Hz and 500 Hz, each group including at least one ultrasonic acquisition.

The repetition rate of the ultrasonic groups is also called inter-group repetition rate.

An ultrasonic acquisition includes the emission of an ultrasonic shot followed by the detection and the recording of the reflected ultrasonic signals or echoes.

The application of a continuous vibration to the viscoelastic medium generates an elastic wave within said medium. The elastic wave includes a superimposition of shear waves and compression waves. The study of the properties of this elastic wave makes it possible to obtain information concerning the correct positioning of the probe with regard to the viscoelastic medium.

The viscoelastic medium to characterise diffuses at least partially the ultrasonic shots. It is thus possible to detect the ultrasonic signals reflected during the emission of the first series of ultrasonic acquisitions.

The detection of the reflected ultrasonic signals may be carried out using the same ultrasonic transducer used for the emission.

An ultrasound attenuation parameter may be determined from the reflected ultrasonic signals. For example the value CAP_I of the ultrasonic attenuation corresponding to a given ultrasonic acquisition may be determined. The value CAP_I is also called individual or instantaneous value of the ultrasonic attenuation or instantaneous ultrasonic attenuation parameter.

The reflected ultrasonic signals detected during the step CW are successively processed during a step of determination of at least one property of the propagation of the elastic wave within the viscoelastic medium CW_P.

Typically, during this step, the reflected ultrasonic signals are correlated with each other so as to measure the displacements of the viscoelastic medium brought about by the elastic wave generated by the application of the continuous vibration, according to a known technique in the field of elastography and more generally ultrasounds.

From the displacements measured within the viscoelastic medium, it is possible to compute properties of the elastic wave such as the amplitude and the phase as a function of the position within the viscoelastic medium. The position of a point within the viscoelastic medium is measured as the distance between the ultrasonic transducer and said point computed along the direction of propagation of the ultrasounds emitted by the transducer. For this reason the position of a point within the viscoelastic medium is generally called depth.

It is also possible to determine other parameters of the elastic wave within the viscoelastic medium, such as the phase velocity or the attenuation of the elastic wave.

The variations in the amplitude and the phase of the elastic wave as a function of depth within the tissue may be computed. By making an adjustment between the theoretical model and the measured properties, it is possible to extract an adjustment quality parameter. From this adjustment quality parameter and/or other properties of the elastic wave, it is possible to compute a positioning indicator RT_IP of the probe with respect to the tissue to characterise.

For example, one of the theoretical models used provides a linear variation of the phase lag at the central frequency of the elastic wave with depth in the medium to characterise. In this case, the adjustment is a linear adjustment and the adjustment quality parameter translates the linearity of the phase as a function of depth in the medium. A possible indicator is the determination coefficient $R^2$ giving the quality of the prediction of the linear regression of the curve of the phase lag as a function of depth in the studied depth range.

According to one embodiment, the step CW_P of determination of at least one property of the elastic wave within the tissue is carried out at the same time as the step of application of the continuous vibration CW and detection of the first reflected ultrasonic signals.

Thanks to the method P according to the invention it is thus possible to measure in real time the properties of the elastic wave within the tissue and to obtain in real time the positioning indicator of the probe RT_IP.

Advantageously, a low repetition rate makes it possible to reduce the size of the data recorded during the step of generation of the series of ultrasonic acquisitions CW and to process these data in real time to obtain the positioning indicator RT_IP. The value of this indicator is typically comprised between 0 and 1. The value 0 corresponds to a poor indicator and the value 1 to a good indicator.

Advantageously, the positioning indicator is provided to the operator to help him to find a satisfactory measurement point. It may be provided for example (non-exhaustive list) in the form of a display of a coloured indicator, in the form of a more or less long bar, etc.

A quality coefficient of the measurement of the ultrasonic attenuation, CAP_C, is also computed from the ultrasonic signal. The value of this coefficient is typically comprised between 0 and 1. The value 0 corresponds to a low quality and the value 1 to a high quality.

The coefficient CAP_C is associated with the individual value of the ultrasonic attenuation CAP_I obtained from the ultrasonic data during acquisition.

The quality coefficient CAP_C may for example be computed from only the properties of the ultrasonic signal. It may also be a combination of the quality of the ultrasonic signal and the properties of the elastic wave.

According to one embodiment, the individual value of the ultrasonic attenuation is only conserved if the positioning indicator RT_IP is correct. In the case where the positioning indicator RT_IP is incorrect, the corresponding coefficient CAP_C is for example set at zero.

According to one embodiment, the continuous vibration is only triggered if the contact force F between the vibrator and the viscoelastic tissue is above a predetermined lower threshold. The value of the threshold is typically 1 N.

Advantageously, this lower threshold ensures sufficient coupling between the probe and the viscoelastic medium.

According to one embodiment, the continuous vibration is only triggered if the contact force F between the vibrator and the viscoelastic tissue is below an upper predetermined threshold. The value of the threshold is typically 10 N.

Advantageously, this upper threshold ensures that the vibration is not deformed and that the studied medium is not damaged.

On account of the continuous vibratory movement of the vibrator, the determination of the contact force F between the vibrator and the medium is more complex than in the case of a standard transient elastography method. In the presence of the continuous low frequency vibration, the contact force between the vibrator and the viscoelastic medium is given by the following formula:

$$F = k(x + A \times \cos(2\pi_{flow} t))$$

In this formula x is the displacement of the vibrator, k the elastic constant of the spring placed in the probe, A the amplitude of the continuous vibration and flow the continuous vibration frequency.

The force F may be measured using a force sensor placed on the hybrid elastography probe. Successively by applying a low pass filter to the signal thereby measured, it is possible to eliminate the low frequency part and to deduce the average contact force:

$$F_{average} = k(x)$$

Advantageously the value of the average force applied is provided to the operator so that he adapts it in order that the low frequency vibration and the acquisition of data continue.

Advantageously the individual values CAP_I are accumulated in a memory and used to compute an average value CAP_M. CAP_M may be computed in several ways.

For example:

$$CAP\_M = \frac{\sum_{i=1}^{N}(CAP\_I(i) \times CAP\_C(i))}{\sum_{i=1}^{N}(CAP\_C(i))}$$

The values CAP_C are then used to weight the individual measured values CAP_I. The value CAP_M is conserved at the end of the examination as being the measured ultrasonic attenuation value. The unit of the value CAP_M is for example dB/m.

Figure 2:
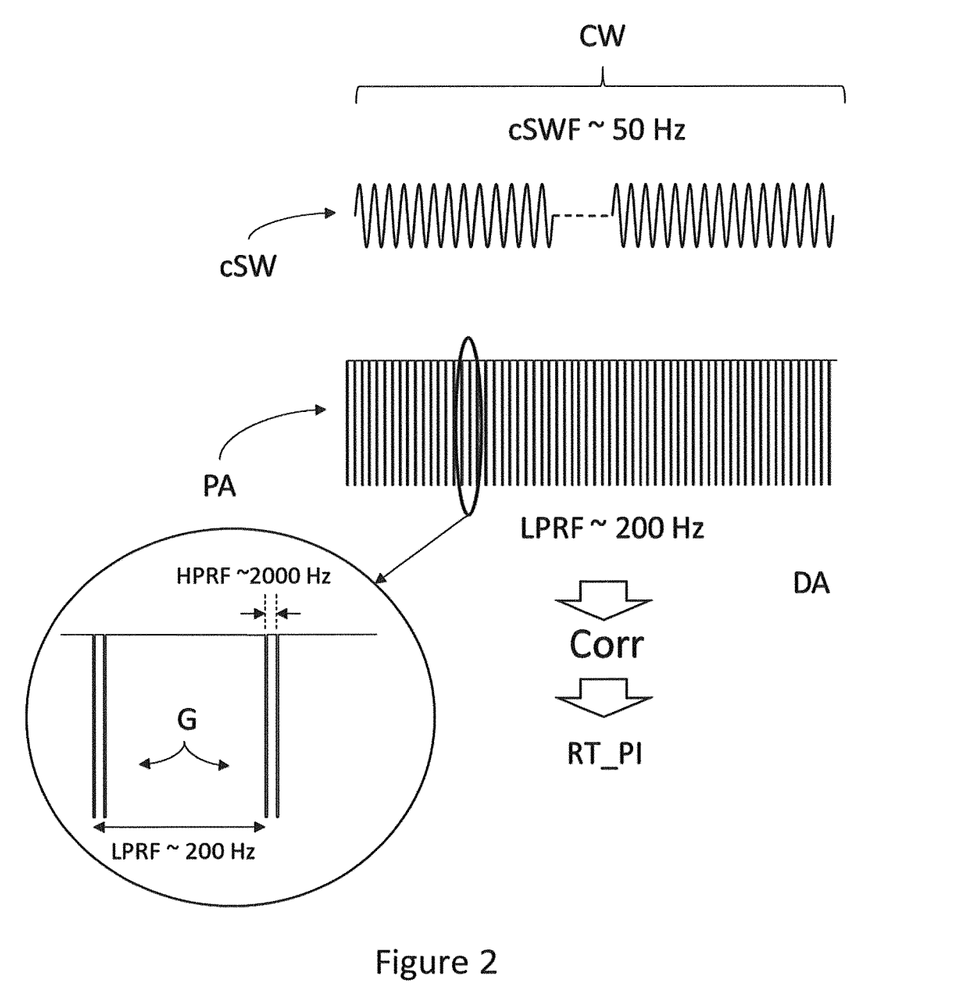
FIG. 2 schematically shows the vibrations applied by the vibrator and the ultrasonic acquisitions during the implementation of the method according to the invention illustrated in FIG. 1.

FIG. 2 schematically shows:
The continuous low frequency vibration cSW applied by the vibrator during the step CW illustrated in FIG. 1;
The series of ultrasonic acquisitions PA formed by the groups G of acquisitions and generated by the ultrasonic transducer during the step CW illustrated in FIG. 1.

During the step of application of a continuous vibration CW, the vibrator oscillates at a frequency comprised between 5 and 500 Hz, with an amplitude comprised between 10 μm and 5 mm.

Advantageously, thanks to the low amplitude and to the low frequency of the continuous vibration, an operator can easily maintain the probe in contact with the viscoelastic medium.

At the same time as the application of the continuous low frequency vibration, the ultrasonic transducer emits ultrasonic acquisitions PA formed by groups G of ultrasonic acquisitions. In the example illustrated in FIG. 2, each group G includes two ultrasonic acquisitions.

The groups G of ultrasonic acquisitions are emitted with a repetition rate LPRF comprised between 10 Hz and 500 Hz or inter-group repetition rate or simply repetition rate. The ultrasonic acquisitions belonging to a same group G are emitted with an intra-group repetition rate HPRF comprised between 500 Hz and 10 kHz. The ultrasonic transducer also detects the ultrasonic signals reflected during the generation of the ultrasonic acquisitions PA, as explained with reference to the step CW illustrated in FIG. 1. From the first series of ultrasonic acquisitions PA, it is possible to compute, by a step of correlation CORR between ultrasonic signals belonging to the same group G, the displacements of the viscoelastic medium. Said displacements of the viscoelastic medium are generated by the propagation of the elastic wave generated by the continuous vibration applied by the vibrator.

It is important to note that a large number of possible ultrasonic sequences for the implementation of this method exist and that the elements indicated do not in any way constitute an exhaustive list of possible fields.

Advantageously, by applying a correlation technique to the ultrasonic acquisitions belonging to a same group G—and thus brought closer in time—it is possible to detect small displacements of the order of 1 μm to 10 μm.

As explained with reference to the step CW_P illustrated in FIG. 1, the displacements of the viscoelastic medium are next used to compute the properties of the elastic wave such as its amplitude and its phase as a function of depth in the medium. By comparing the measured properties with a theoretical model it is possible to deduce in real time a positioning indicator RT_IP.

For example, the positioning indicator may be linked to the linearity of the phase of the elastic wave as a function of depth in the medium to characterise. The indicator then depends on the quality of the adjustment of the evolution of the phase as a function of depth by a straight line.

For example, the positioning indicator may be linked to the decrease in the amplitude of the elastic wave as a function of depth in the medium to characterise. The indicator then depends on the quality of the fit in $1/Z^n$ where Z is the depth and n an integer coefficient comprised between 1 and 3.

For example, the value of the real time positioning indicator RT_IP is comprised between 0 and 1, with values close to 1 if the probe is correctly positioned with respect to the viscoelastic medium of interest.

Figure 3:
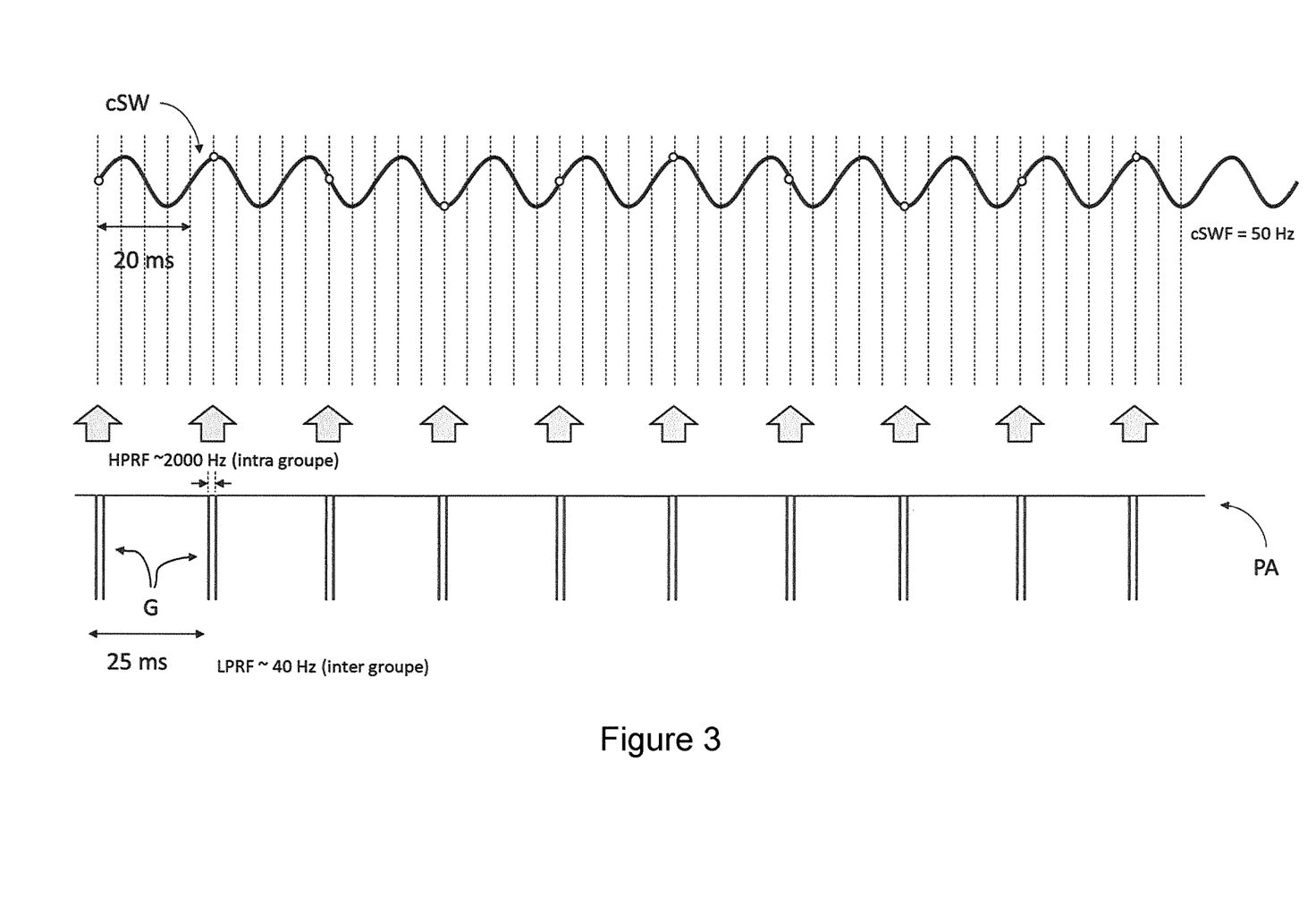
FIG. 3 schematically shows a particular embodiment of the elastography method illustrated in FIG. 1, called stroboscopic mode.

FIG. 3 shows a particular embodiment of the steps CW and CW_P of the method P according to the invention, called stroboscopic mode.

The continuous sinusoidal line schematically represents the continuous vibration cSW applied by the first vibrator. The continuous vibration cSW has for example a central frequency cSWF of 50 Hz corresponding to a period of 20 ms.

The continuous vertical lines represent the groups G of ultrasonic acquisitions forming the first series of ultrasonic acquisitions PA. The groups G are emitted with a first repetition rate LPRF. According to the stroboscopic acquisition mode, the first repetition rate LPRF is smaller than the central frequency of the continuous vibration cSWF.

The intra-group repetition rate is comprised between 500 Hz and 100 kHz, which makes it possible to measure small displacements of the order of 1 μm.

The white circles and the arrows along the continuous vibration cSW correspond to the samplings made by each group G of ultrasonic acquisitions.

Thanks to the fact that the repetition rate LPRF of the groups G is less than the central frequency of the continuous vibration cSW, it is possible to sample in a complete manner the continuous vibration cSW at the end of several oscillation periods, as is illustrated by the white circles.

Advantageously, the stroboscopic mode makes it possible to sample in a complete manner the continuous vibration cSW while using a low first repetition rate LPRF.

The use of a low repetition rate makes it possible to process the reflected signals in real time and thus to obtain the positioning indicator RT_IP in real time.

Figure 4:
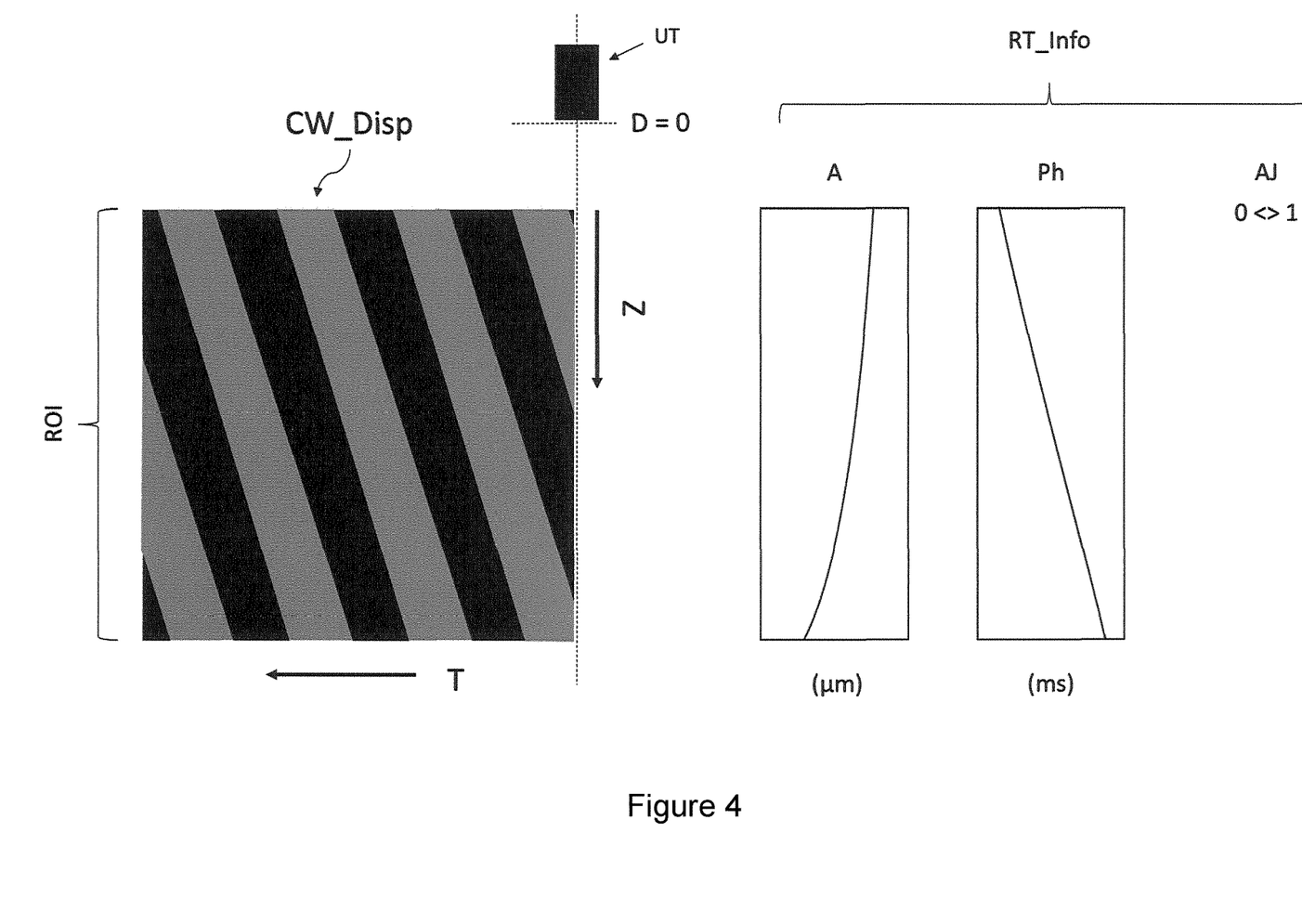
FIG. 4 shows the results obtained by implementing the part of the method according to the invention relative to the positioning of the vibrator.

FIG. 4 schematically shows the results obtained by implementing the part of the method P according to the invention relative to the positioning of the vibrator.

The graph CW Disp shows the displacement (or any other movement parameter such as the velocity, the deformation, the deformation rate) of the viscoelastic medium in a region of interest ROI as a function of depth Z in the medium and of time T. The displacements are represented using a false colour scale, the lighter colours representing a displacement along the positive direction of the axis D. The displacements are caused by the continuous low frequency vibration applied by the vibrator and are measured by the ultrasonic transducer UT placed in contact with the surface of the medium, in Z=0.

From the displacements measured CW Disp in the region of interest ROI within the viscoelastic medium, it is possible to extract in real time information RT_Info concerning the elastic wave propagating within the medium and generated by the continuous vibration. Examples of such properties are amplitude A and phase Ph of the elastic wave as a function of depth within the medium.

By comparing the values of A and Ph measured with predetermined thresholds it is possible to determine a positioning indicator of the vibrator with respect to the viscoelastic medium.

Alternatively, it is possible to obtain an adjustment quality parameter AJ between the measured quantities A and Ph and a theoretical model describing the amplitude and phase of an elastic wave propagating within the medium. In this case, the positioning indicator is obtained from the adjustment quality parameter AJ. For example, an adjustment quality parameter is the determination coefficient $R^2$ giving the quality of the prediction of the linear regression of the curve of the phase lag as a function of depth in the studied depth range.

According to one embodiment, the adjustment quality parameter AJ is comprised between 0 and 1.

Once calculated, the positioning indicator may be displayed in the form of a number or a letter or by using a colour scale. Alternatively, the positioning indicator may be a simple visual indication of the disc type colourful. Alternatively, the positioning indicator may be a simple visual indication of "Positioning OK" type indicating that the operator can trigger the transient elastography step.

According to one embodiment, the propagation velocity of the elastic wave is conserved as a measurement of the elasticity of the medium.

During the implementation of the method P according to the invention, the graphs CW_Disp, RT_Info and the positioning indicator of the vibrator are computed and displayed concomitantly.

Advantageously, thanks to the structure of the series of ultrasonic acquisitions, the positioning indicator RT_IP as well as the graph RT_Info may be computed and displayed in real time.

Figure 5:
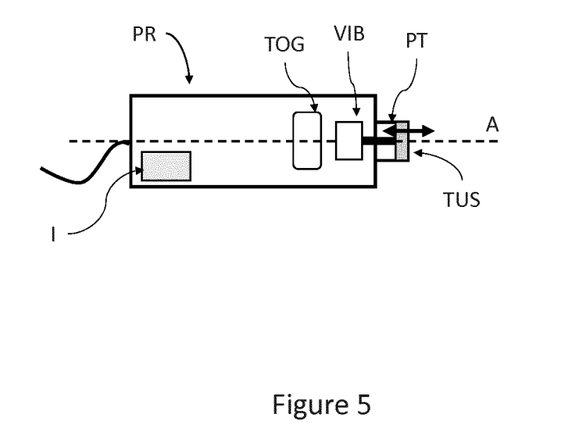
FIG. 5 represents a hybrid elastography probe according to the invention.

FIG. 5 schematically represents a probe PR for the measurement of the ultrasonic attenuation guided by harmonic elastography.

The probe PR includes:
A vibrator VIB configured to apply to the viscoelastic medium a continuous low frequency vibration, the continuous low frequency vibration generating an elastic wave within the viscoelastic medium;
An ultrasonic transducer TUS configured to emit a series of ultrasonic acquisitions, said series of ultrasonic acquisitions including groups of ultrasonic acquisitions, the groups of ultrasonic acquisitions being generated with a repetition rate, each group of ultrasonic acquisitions including at least one acquisition.

According to the embodiment illustrated in FIG. 1, the ultrasonic transducer TUS is mounted on the axis of the vibrator VIB.

According to one embodiment, the probe PR includes computing means for computing in real time the positioning indicator RT_IP from the ultrasonic acquisitions.

According to one embodiment, the probe PR includes means for computing and displaying the real time positioning indicator RT_IP.

According to one embodiment, the refresh rate of the display of the positioning indicator is greater than 5 Hz.

Advantageously, the display of the real time positioning indicator at the level of the probe allows the operator to optimise the positioning of the probe without diverting his eyes from the probe and from the body of the patient. This simplifies the operation of positioning the probe.

According to one embodiment, the ultrasonic transducer TUS may be fixed to the body of the probe using a tip PT.

The vibrator VIB makes the probe PR oscillate. During this oscillation, the ultrasonic transducer TUS is pushed against the viscoelastic medium applying the continuous low frequency vibration and creating the elastic wave within the medium.

According to one embodiment, the vibrator VIB for the application of the low frequency vibration includes a vibratory ring placed around the ultrasonic transducer TUS or around the probe tip PT.

According to one embodiment, the probe tip PT is moveable and may be actuated by the vibrator VIB. The ultrasonic transducer TUS is then pushed against the viscoelastic medium to apply the vibration, along the direction of the arrow of FIG. 5

Figure 6A:
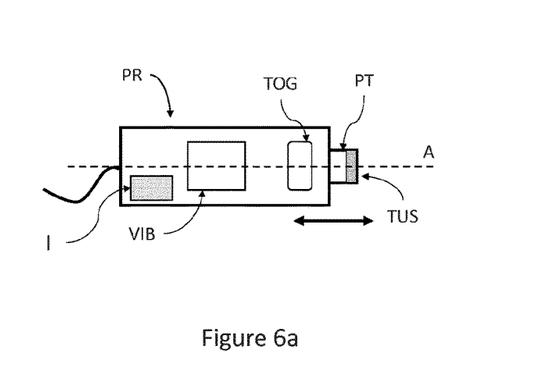
FIG. 6a represents a particular embodiment of the hybrid elastography probe according to the invention.

According to a second embodiment, illustrated in FIG. 6a, the probe PR is an inertial probe without external moving parts. In this case, the movement of the vibrator VIB within the probe PR leads to the movement of the probe and the continuous or pulsed vibration is once again applied by pushing the transducer TUS against the viscoelastic medium.

The axis of movement of the vibrator VIB is preferably an axis A of symmetry of the ultrasonic transducer TUS. For example, the ultrasonic transducer TUS may have a circular section, the axis A passing through the centre of the ultrasonic transducer TUS.

According to one embodiment, the probe PR includes control means TOG for triggering the measurement.

The probe PR according to FIGS. 5 and 6a thus includes a vibrator VIB intended to apply the continuous low frequency vibration.

According to one embodiment, the diameter of the ultrasonic transducer is comprised between 2 and 15 mm.

According to one embodiment, the central frequency of the ultrasonic transducer is comprised between 1 MHz and 15 MHz.

According to one embodiment, the ultrasonic transducer TUS is a convex abdominal probe.

According to one embodiment, the probe includes a positioning indicator which is triggered when the probe is correctly positioned. This indicator may be a visual indicator, for example a change of colour of diodes. Alternatively, the indicator may be a sound or haptic indicator such as a change of type or amplitude of a vibration.

Figure 6B:
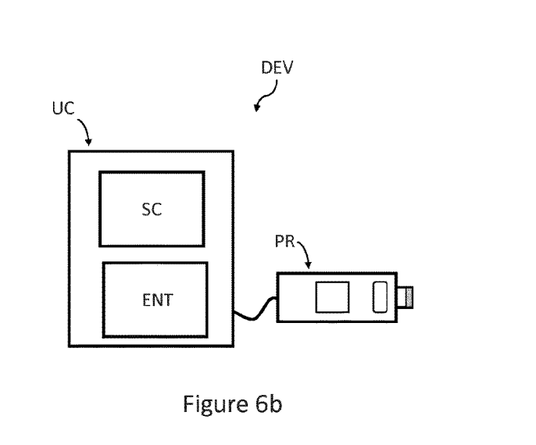
FIG. 6b represents a hybrid elastography device according to the invention.

FIG. 6b illustrates a hybrid elastography device DEV according to the invention.

The device DEV according to the invention includes:
A probe PR according to the invention;
A central unit UC connected to the probe PR.

The central unit may comprise:
Computing means for processing the reflected ultrasonic signals;
A screen SC for displaying the results obtained at the different steps of the method P according to the invention;
Control or input means ENT for the control of the device by the operator.

The central unit UC may be connected to the probe PR by a wire link or by wireless communication means.

According to one embodiment, the screen SC is suited for the display of the results illustrated in FIG. 4. The screen SC may also display in real time the position indicator RT_IP computed during the step CW_P of the method P according to the invention.

According to one embodiment, the central unit includes means configured to trigger automatically the application of a low frequency pulse on the basis of the value of the positioning indicator RT_IP computed and displayed in real time.

According to one embodiment, the central unit is comprised in the probe PR.

The invention claimed is:

1. A method for measuring an ultrasonic attenuation parameter guided by harmonic elastography comprising applying, using a vibrator comprised in a probe in contact with a viscoelastic medium, a continuous low frequency vibration, the continuous low frequency vibration generating an elastic wave within the viscoelastic medium and generating, during the propagation of the elastic wave, using an ultrasonic transducer in contact with the viscoelastic medium, a series of ultrasonic acquisitions, said series of ultrasonic acquisitions including groups of ultrasonic acquisitions, the groups of ultrasonic acquisitions being generated with a repetition rate, each group of ultrasonic acquisitions including at least one acquisition, the ultrasonic attenuation parameter being measured from the ultrasonic acquisitions.

2. The method for measuring an ultrasonic attenuation parameter guided by harmonic elastography according to claim 1, further comprising determining, from the series of ultrasonic acquisitions, at least one property of the propagation of the elastic wave within the viscoelastic medium.

3. The method for measuring an ultrasonic attenuation parameter guided by harmonic elastography according to claim 2, wherein the property of the propagation of the elastic wave within the viscoelastic medium is used to compute a real time positioning indicator of the probe compared to the viscoelastic medium to study.

4. The method for measuring an ultrasonic attenuation parameter guided by harmonic elastography according to claim 3, further comprising displaying in real time the real time positioning indicator.

5. The method for measuring an ultrasonic attenuation parameter guided by harmonic elastography according to claim 2, wherein the propagation property of the measured elastic wave is selected from one of amplitude of the elastic wave, phase of the elastic wave, phase velocity of the elastic wave, elasticity of the viscoelastic medium, Young's modulus of the viscoelastic medium and shear modulus of the viscoelastic medium.

6. The method for measuring an ultrasonic attenuation parameter guided by harmonic elastography according to claim 1, wherein the application of a continuous low frequency vibration is only triggered if the contact force between the vibrator and the viscoelastic medium is above a predetermined lower threshold.

7. The method for measuring an ultrasonic attenuation parameter guided by harmonic elastography according to claim 1, wherein the application of a continuous low frequency vibration is only triggered if the contact force between the vibrator and the viscoelastic medium is above a predetermined lower threshold and below a predetermined upper threshold.

8. The method for measuring an ultrasonic attenuation parameter guided by harmonic elastography according to claim 1, wherein the series of ultrasonic acquisitions is formed by a repetition of groups including at least two ultrasonic acquisitions having an intra-group repetition rate comprised between 500 Hz and 10 kHz and a repetition rate comprised between 10 Hz and 10 kHz.

9. The method for measuring an ultrasonic attenuation parameter guided by harmonic elastography according to claim 1 wherein the repetition rate is lower than a frequency of the continuous low frequency vibration.

10. The method for measuring an ultrasonic attenuation parameter guided by harmonic elastography according to claim 1, wherein the ultrasonic attenuation parameter is an instantaneous parameter and a quality coefficient associated with the measurement of the instantaneous ultrasonic attenuation parameter is computed from a property of the propagation of the elastic wave within the viscoelastic medium and/or properties of the ultrasonic wave.

11. The method for measuring an ultrasonic attenuation parameter guided by harmonic elastography according to claim 10, wherein an average ultrasonic attenuation parameter is computed from a plurality of instantaneous ultrasonic attenuation parameters and quality coefficients associated with each instantaneous ultrasonic attenuation parameter.

12. A probe for measuring an ultrasonic attenuation parameter guided by harmonic elastography comprising:
 a vibrator configured to apply to the viscoelastic medium a continuous low frequency vibration, the continuous low frequency vibration generating an elastic wave within the viscoelastic medium;
 an ultrasonic transducer configured to emit a series of ultrasonic acquisitions, said series of ultrasonic acquisitions including groups of ultrasonic acquisitions, the groups of ultrasonic acquisitions being generated with a repetition rate, each group of ultrasonic acquisitions including at least one acquisition;
 a system adapted to compute and display in real time a positioning indicator of the probe, said positioning indicator being computed from a propagation property of the elastic wave, said propagation property of the elastic wave being determined from the series of ultrasonic acquisitions;
 the ultrasonic attenuation parameter being measured from the ultrasonic acquisitions realised during the application of the continuous low frequency vibration.

13. The probe for measuring an ultrasonic attenuation parameter guided by harmonic elastography according to claim 12, said probe being further configured to apply the continuous vibration when the contact force between the probe and the viscoelastic medium is above a predetermined value.

14. The probe for measuring ultrasonic attenuation parameter guided by harmonic elastography according to claim 12, wherein the transducer is borne by the vibrator.

15. The probe for measuring an ultrasonic attenuation parameter guided by harmonic elastography according to claim 13 configured to compute an average ultrasonic attenuation parameter, said average ultrasonic attenuation parameter being computed from a multiplicity of instantaneous ultrasonic attenuation parameters and quality coefficients associated with the instantaneous ultrasonic attenuation parameters.

16. A device for measuring an ultrasonic attenuation parameter guided by harmonic elastography comprising:
 a probe for measuring of the ultrasonic attenuation guided by harmonic elastography according to claim 12, and
 a central unit connected to the probe and including at least computing system for processing reflected ultrasonic signals, a display and a control and/or input system.

* * * * *